United States Patent [19]
Jones

[11] Patent Number: 5,505,056
[45] Date of Patent: Apr. 9, 1996

[54] METHOD AND APPARATUS FOR STERILIZATION

[76] Inventor: Steven M. Jones, 54 Depot St., Dunstable, Mass. 01827

[21] Appl. No.: 327,002

[22] Filed: Oct. 21, 1994

[51] Int. Cl.$^6$ ............................... F24F 3/16; A23C 3/00
[52] U.S. Cl. .................... 62/78; 62/100; 62/64; 426/320; 426/524
[58] Field of Search .................. 62/64, 78, 100; 426/320, 524

[56] References Cited

U.S. PATENT DOCUMENTS

| | | | |
|---|---|---|---|
| 3,150,497 | 9/1964 | Beckmann | 62/100 X |
| 4,667,478 | 5/1987 | Jones, III | 62/100 X |
| 4,976,920 | 12/1990 | Jacob | 422/23 |
| 5,027,546 | 7/1991 | Tallon | 43/124 |
| 5,115,166 | 5/1992 | Campbell et al. | 422/21 |
| 5,171,525 | 12/1992 | Jacob | 422/23 |
| 5,178,829 | 1/1993 | Moulton et al. | 422/23 |
| 5,186,893 | 2/1993 | Moulton et al. | 422/23 |
| 5,193,350 | 3/1993 | Tallafus | 62/64 |
| 5,200,158 | 4/1993 | Jacob | 422/292 |
| 5,213,759 | 5/1993 | Castberg et al. | 422/24 |
| 5,223,217 | 6/1993 | Frizziero | 422/26 |
| 5,254,309 | 10/1993 | Felix et al. | 422/34 |

*Primary Examiner*—Christopher Kilner
*Attorney, Agent, or Firm*—Pearson & Pearson

[57] ABSTRACT

An apparatus and method for sterilizing items includes a sterilizing chamber that is evacuated. A refrigerant in liquid form expands within the evacuated chamber and rapidly reduces the temperature on the surface of any of the items within the chamber. Thereafter the temperature may rapidly return to room temperature. The rapid temperature changes effectively kill any organisms at or near the surface of any of the items within the chamber.

13 Claims, 2 Drawing Sheets

METHOD AND APPARATUS FOR STERILIZATION

BACKGROUND OF THE INVENTION

1. Field of the Invention

This invention relates to a process for sterilizing a articles and more specifically to a method and apparatus for sterilizing articles by subjecting them to one or more rapid temperature changes.

2. Description of Related Art

Several years ago the process of sterilizing different articles, particularly medical devices, involved immersing the articles in a disinfectant or inserting the articles into an autoclave. Gas sterilization and irradiation processes have has subsequently been introduced, but with only limited acceptance. Ethylene-oxide, for example, is a disinfecting gas, but has been classified as a carcinogen and mutant. Apparatus required for irradiation can subject workers and the environment to safety hazards.

U.S. Pat. No. 5,213,759 (1993) to Castberg et al. discloses a sterilizing method utilizing ultraviolet radiation. Apparatus directs UV energy to a surface immersed in an inert gas to render micro-organisms non-viable.

U.S. Pat. No. 5,223,217 (1993) to Frizziero discloses a sterilization process by which a device for filling syringes is subjected to washing and sterilizing steam. A sterile gas, such as sterile nitrogen, is supplied after the steam sterilization process elevates the temperature to a predetermined value. This sterile gas remains in contact with all the sterilized surfaces until subsequent use.

U.S. Pat. Nos. 4,976,920 (1990), 5,171,525 (1992) and 5,200,158 (1993) to Jacob disclose methods and apparatus for dry sterilization of medical devices. In accordance with these methods, items to be sterilized are located in a vacuum chamber that has a nominal operating pressure of less than 1 torr. RF energy supplied to a coil within the cavity produces a discharge with hydrogen or oxygen as a reducing or oxidizing gas respectively. The interaction with the excited molecular and atomic species formed by this interaction produces low temperature plasma that sterilizes items it contacts.

Related U.S. Pat. Nos. 5,115,166 (1992) to Campbell et al., 5,178,829 (1993) to Moulton et al. and 5,186,893 (1993) to Moulton et al. disclose the use of plasma for sterilization. Generally each of these patents discloses sterilization by exposure of an article to a plasma generated from a gas mixture that can be argon, helium, nitrogen or mixtures thereof with a mixture of hydrogen or oxygen. The plasma is generated in a vacuum chamber with an operating pressure of less than 10 torr for a time period sufficient to effect sterilization. In U.S. Pat. No. 5,178,829, in particular, the process is modified to provide gas sterilization by subjecting articles to the gas plasma until the temperature in the sterilizing chamber rises to a preselected maximum. The flow of plasma gas to the sterilizing chamber then terminates until the temperature in the sterilizing chamber falls below a preselected value. These steps repeat until sterilization is effected. The pressure in the chamber varies from 0.1 to 10 torr.

Each of the foregoing sterilization methods operate effectively. However, the use of special gases introduces a requirement for obtaining and handling those gases in the operating environment. The RF sources used in certain of these processes particularly for generating plasmas and ultraviolet energy, must be properly shielded in order to avoid disturbance of any proximate RF-sensitive equipment. These plasma processes also operate in a so-called high vacuum range of 10 torr or less that may require special chambers and vacuum pumping systems. After the sterilization process is completed, care must be taken of disposing of residual gases particularly where significant quantities of ionized gas may be present.

SUMMARY

Therefore it is an object of this invention to provide a method and apparatus for sterilizing items in which the apparatus is self-contained and does not require any special gases.

Another object of this invention is to provide a method and apparatus for sterilizing items which operate without any requirement for, producing high-power radio frequencies or high-voltage discharges.

Still another object of this invention is to provide a method and apparatus for sterilizing items that does not produce toxic residues.

Yet another object of this invention is to provide a method and apparatus for sterilizing items within a minimal time.

Still yet another object of this invention is to provide a method and apparatus for sterilizing items that is effective and simple to operate.

In accordance with this invention, items are located in a sterilization chamber that then is placed under a partial vacuum and liquid refrigerant is supplied to an expansion valve. After the partial vacuum is drawn, the liquid refrigerant flows into the chamber through an expansion valve. As the liquid expands, it dramatically reduces the temperature within the vacuum chamber to or below the boiling point of the liquid refrigerant. Thereafter heated air under pressure can be admitted to elevate the temperature back to room temperature and the pressure back to atmospheric pressure thereby to complete the sterilization process.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
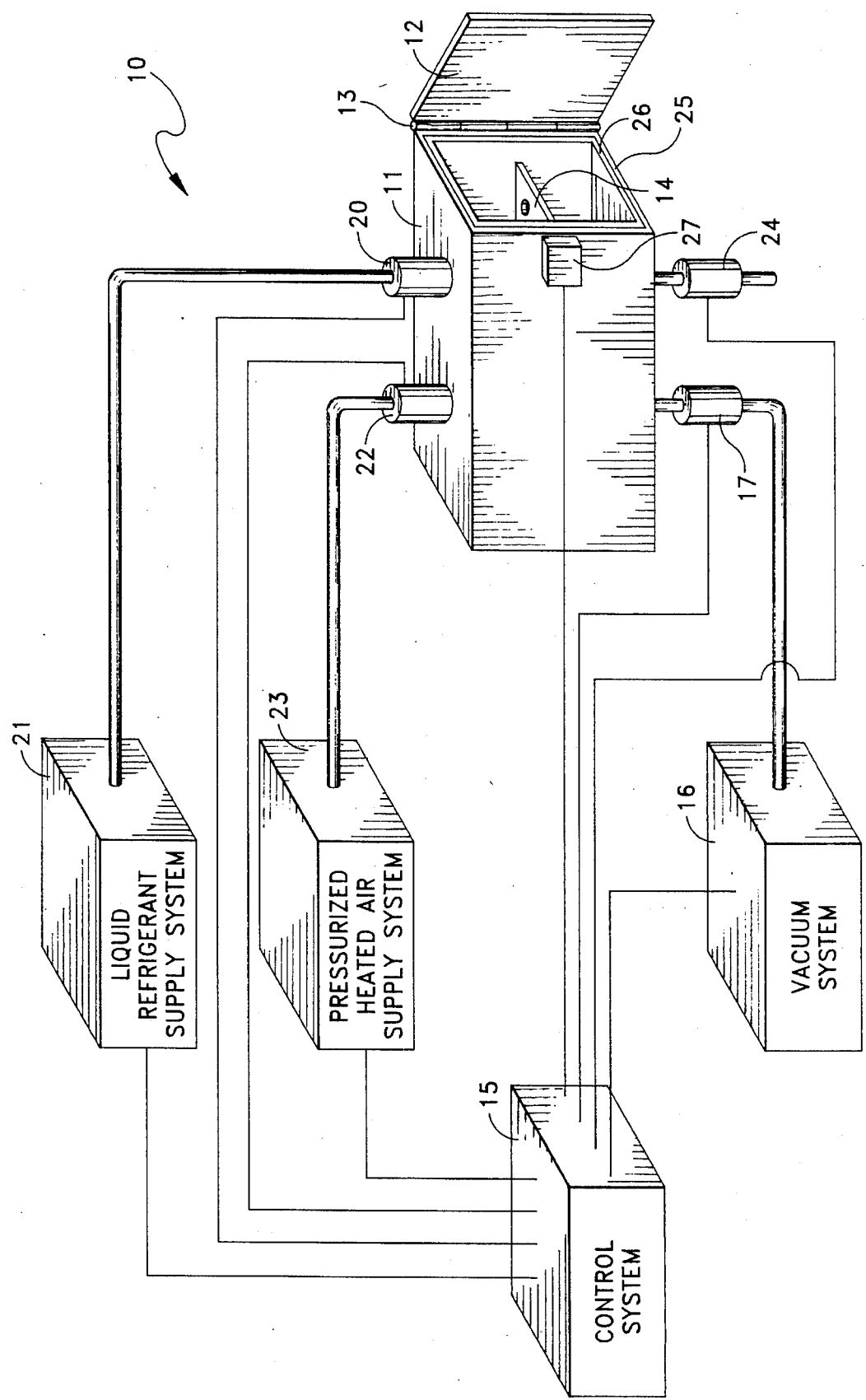
FIG. 1 is a diagram depicting, in block form, the major components of apparatus for performing the sterilization method of this invention.

Referring to FIG. 1, sterilizing apparatus 10 constructed in accordance with this invention includes a sterilizing chamber 11 having a door 12 mounted on a hinge 13 such that the door 12 can close on the chamber 11 and allow a vacuum to be pumped within the chamber 11. The chamber may include one or more perforated shelves 14 for storing items in tiers. Once the door 12 closes, a control system 15 initiates the operation of a vacuum system 16 and opens the vacuum valve 17 and produces a vacuum within the closed chamber 11. Typically the vacuum system 16 will lower the pressure to about 0.1 ATM (i.e., 76 torr). Once the vacuum reaches a predetermined level, the control system 15 isolates the vacuum system 16 from the sterilizing chamber 11 and opens an expansion valve 20 that receives a refrigerant in liquid form, such as liquid nitrogen, from a liquid refrigerant supply 21. When this occurs, the liquid refrigerant expands into a gas within the sterilizing chamber 11. Consequently the temperature drops rapidly toward the boiling point of the liquid refrigerant and, due to the partial pressure within the chamber as the gas is admitted, toward a final temperature which is even below the boiling point of the liquid refrigerant. This reduces the surface temperature on any items that the gaseous refrigerant contacts to a temperature at or below the boiling point. Admitting liquid nitrogen can produce a temperature drop of 400° F. within an interval of about 15 seconds. This rapid temperature decrease over this short of interval kills any living organisms on or near the surface.

After this interval, the control system 15 turns off the valve 20 and opens a valve 22 that conducts pressurized heated air from a pressurized heated air supply 23 into the sterilization chamber 11. The control system 15 monitors the pressure to operate a pressure relief valve 24 if the pressure within the sterilizing chamber 11 exceeds a predetermined value. The heated pressurized air raises the temperature within the chamber to approximately room temperature and the pressure returns to atmospheric pressure. The door 12 then can be released and the sterilized items removed.

Referring now to each assembly, the sterilization chamber 11, as shown in FIG. 1, is formed as a vacuum chamber for withstanding pressure reductions in the order of 0.1 ATM. The chamber can have a rectangular shape as shown or a cylindrical shape as required. The tank can be formed of a metal, such as aluminum or stainless steel, of a ceramic or of a composite of an outer metal structure for strength and a ceramic liner for heat insulation.

The door 12 forms a vacuum seal with an edge 25 of the chamber 11 facing the door 12. The edge 25 carries a sealing O-ring 26 circumscribing the door aperture. A sensor 27 monitors door position and provides and indication of door closure. Latches or other mechanisms, that are not shown but are well known in the art, can be utilized to mechanically hold the door in a closed position until the vacuum system 16 begins to operate.

Figure 2:
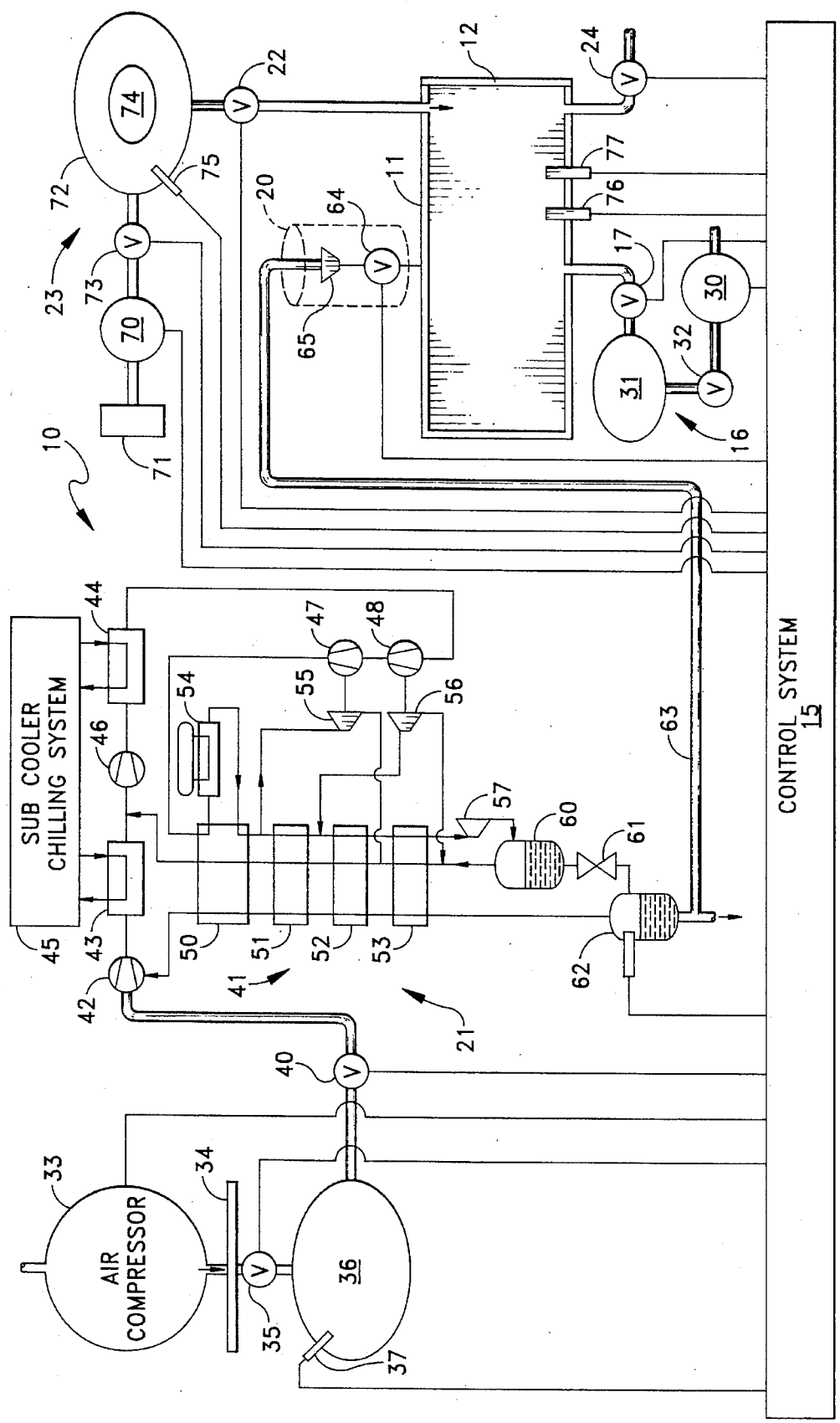
FIG. 2 depicts the apparatus in FIG. 1 schematically.

Referring to FIG. 1, and particularly to FIG. 2, the vacuum system 16 comprises a standard vacuum pump 30 that initially pumps a tank 31 through a standard gate valve 32 and, when the gate valve 17 is open, pumps the interior of the sterilization chamber 11. The gate valve 32 may be manual or operated by the control system 15.

In operation, the control system will initiate vacuum pumping by closing the valve 17 and operating the pump 30 to partially evacuate the tank 31. Then the control system 15 will open the valve 17 to allow evacuation of the sterilization chamber 11. Once the pressure has reached a predetermined level in the range of 0.1 ATM (i.e., 76 torr) the valve 17 closes thereby isolating the vacuum system 16 from the sterilization chamber 11. As will be apparent a standard mechanical vacuum pump typically can achieve these vacuums so this apparatus does not require a high vacuum pumping system with its attendant cooling.

A preferred embodiment of the liquid refrigerant supply system 21 shown in FIG. 1 and in more detail in FIG. 2, is a self-contained liquid nitrogen generator that does not require an external source. In the liquid refrigerant supply system 21 shown in FIG. 2, an air compressor 33 supplies air under pressure to one surface of a direct air-to-nitrogen conversion membrane 34 of conventional design. A valve 35 conveys the nitrogen from the membrane 34 into a storage tank 36. The control system 15 monitors the pressure within the tank 36 by means of a pressure sensor 37 to control the compressor 33. A valve 40 transfers gaseous nitrogen into a conventional nitrogen liquification unit 41 that includes a nitrogen compressor 42 and subcoolers 43 and 44. A dedicated subcooler chiller or refrigeration system 45 can connect heat exchangers in to the subcoolers 43 and 44 to provide a self-contained unit. Chilled liquid can also be admitted through the heat exchangers from a separate source. The unit 41 additionally includes recirculating nitrogen compressors 46, 47 and 48 and heat exchangers 50, 51, 52 and 53. A refrigeration unit 54 connects in the loop associated with the heat exchanger 50. Expansion tubes 55 and 56 couple the recirculating compressors 47 and 48 into the lines between the various heat exchangers. A final expansion valve 57 transfers liquid refrigerant into a first of two storage vessels 60 and a valve 61 couples additional liquid into a second vessel 62 thereby to provide liquid nitrogen at the output of the vessel 62 and in a conduit 63 that connects to the expansion valve 20.

When the control system 15 senses a sufficient supply of liquid refrigerant within the liquid refrigerant supply 21 and has isolated the sterilization chamber 11 at a reduced pressure by closing the valve 17, it operates the expansion valve 20 that includes a gate valve 64 and an expansion orifice 65 located at the sterilization chamber 11. Consequently the gas enters the sealed sterilization chamber 11 and expands under the reduced pressure within the tank chamber 11 to produce a temperature drop toward or below the boiling point for nitrogen, a drop of over 200° C. or 400° F. The control system 15 allows nitrogen to expand into the sterilization chamber for a period of about 15. Again, the resulting rapid temperature decrease will effectively kill any microorganisms at the surface of any item within the sterilization chamber 11.

Once this cooling operation terminates, the control system 15 could merely vent air into the system through the valve 24 or the like. However, in a preferred form of this invention, the control system 15 admits heated air under pressure into the chamber 11 to raise the temperature rapidly to approximately room temperature to kill any organisms that may have survived the temperature decrease. More specifically, the pressurized heated air supply 23 comprises an air compressor 70 that receives air through an optional filter 71 and connects to a pressure tank 72 through a valve 73. A heater 74 located within the pressure tank 72 heats the air to a predetermined temperature. A sensor array 75 attached to the tank 72 allows the control system 15 to monitor the pressure and temperature within the tank 72. The control system 15 normally will initiate the operation of the air compressor 70 and heater 74 when the door 12 closes, simultaneously with the beginning of vacuum pumping. During this interval the valves 22 and 24 are closed. When the control system 15 terminates the admission of nitrogen by closing the valve 20, the valve 22 opens and the heated air under pressure is admitted into the tank. Air temperatures of about 800° F. and pressures in the range of 75 to 100 psi are preferred.

A temperature sensor 76 and a pressure sensor 77 provide information for terminating the sterilization operation and for opening the valve 24. More specifically, when the air within the pressure tank 11 reaches a temperature of about room temperature, the control system 15 opens the valve 24 and vents the interior of the sterilization chamber 11. Normally this will occur before the pressure within the chamber rises significantly. The pressure sensor 77, that may be a separate pressure sensor as shown in FIG. 2 or formed integrally with the valve 24, provides over pressure protection.

Thus the sterilization process or method in accordance with this invention includes locating items to be sterilized in the chamber 11. After the door 12 closes, the control system 15 initiates three basic operations simultaneously. First, it energizes the vacuum system 16 to begin to reduce the pressure within the sterilization chamber 11 to a pressure in the range of about 0.1 ATM. Second, it monitors the liquid refrigerant supply 21 to assure an adequate supply of refrigerant in liquid form, such as liquid nitrogen, at an expansion valve 20. Third, it energizes the pressurized heated air supply to start to produce a supply of air at about 800° F. and a pressure of 70 to 100 psi.

When the predetermined vacuum level is achieved and the available supplies of liquid refrigerant and heated air are available, the control system 15 closes the valve 17 operates the valve 64 admitting liquid nitrogen into the evacuated sterilization chamber 11 producing the approximate 400° F. drop temperature within 15 seconds that essentially kills any microorganisms that are on the surfaces of any of the items within the chamber 11. In a preferred form of the invention, the control system 15 thereafter closes the valve 20 and opens the valve 22 to produce a rapid temperature rise through the same temperature range under the influence of the pressurized heated air supply 23. The air itself will be sterile due to the 800° temperature within the tank 72. This process again takes about 15 seconds and destroys any organisms that may have survived the preceding temperature drop.

As will now be apparent, each of the vacuum system 16, liquid refrigerant supply 20 and heated air supply 23 operates in sequence and through a series of simple monitoring and valve actuation steps. Consequently the control system 15 is readily implemented by a conventional programmable controller or other simple computer-operated system that will, with appropriate displays and sensors according to techniques known in the art, provide the necessary control and operating functions in the appropriate sequences.

Thus in accordance with the objects of this invention, the apparatus shown in FIGS. 1 and 2 is self-contained. No separate inert gas supplies are needed. All the gases are taken from the atmosphere, although the liquid refrigerant supply could be constituted by an external liquid nitrogen supply if desired. The system operates without producing any RF energy or high voltage discharges. There are no toxic gases and no toxic residues produced. Finally the system is adapted for simple reliable operation and provides a rapid sterilization of any items within the system.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. Apparatus for sterilizing items comprising:
  (A) a sterilizing chamber having a sealable door thereon for allowing the introduction of items into the tank,
  (B) vacuum means for attachment to said sterilizing chamber,
  (C) first supply means for an expandable refrigerant in liquid form,
  (D) controllable vacuum valve means for enabling said vacuum means to produce a vacuum in said sterilizing chamber when said door is closed,
  (E) controllable expansion valve means for admitting the refrigerant into said sterilizing chamber, the refrigerant expanding upon entering said sterilizing chamber,
  (F) control means connected to said sterilizing chamber, said vacuum means, said first supply means, and said plurality of valve means for causing said vacuum valve means and said controllable expansion valve means to operate in a sequence whereby the liquid refrigerant expands in said sterilization chamber under vacuum thereby to produce a rapid temperature decrease, and
  (G) said vacuum means includes a vacuum tank, a vacuum pump for evacuating said vacuum tank and wherein said controllable vacuum valve means is intermediate said vacuum tank and said sterilizing chamber.

2. Sterilization apparatus as recited in claim 1 wherein vacuum means additionally includes vacuum sensing means and said control means initiates operation of said vacuum means by causing said controllable vacuum valve means to open thereby to evacuate said sterilizing chamber when said door is closed, said control means terminating operation by causing said controllable vacuum valve means to close when said vacuum sensing means indicates that the pressure within said sterilizing chamber has reached a predetermined value.

3. Sterilization apparatus as recited in claim 1 wherein said first supply means includes means for producing a liquified gas from the atmosphere and means for conveying the liquified gas to said controllable expansion valve means.

4. Sterilization apparatus as recited in claim 3 wherein said control means includes means for producing with said vacuum means a predetermined pressure within said sterilization chamber and means for thereafter causing said controllable expansion valve means to operate thereby allowing the liquified gas to expand within said sterilizing chamber and reduce the temperature within said sterilizing chamber rapidly.

5. Sterilization apparatus as recited in claim 4 wherein said means for producing said liquified gas includes:
  (i) a direct air-to-nitrogen conversion system having an input and an output,
  (ii) means for delivering air under pressure to said input,
  (iii) storage tank means connected to said output, and
  (iv) liquification means for converting said compressed gas in said storage tank means into a liquified gas.

6. Sterilizing apparatus as recited in claim 3 additionally comprising:
  (A) second supply means for providing heated gas under pressure, and
  (B) controllable heated gas valve means for admitting heated air into said sterilizing chamber, said control means being additionally connected to said second supply means and said controllable heated gas valve means for causing said controllable heated gas valve means to operate in sequence after said controllable expansion valve means thereby to subject the items in said sterilization chamber are subject to a rapid temperature increase.

7. Sterilization apparatus as recited in claim 6 wherein second supply means includes means pressure tank means, compressor means for storing air in said pressure tank means under pressure and heater means in said pressure tank means for heating the air therein and wherein said controllable heated gas valve means is intermediate said pressure tank and said sterilization chamber.

8. Sterilization apparatus as recited in claim 7 additionally comprising controllable pressure relief valve means connected to said sterilization chamber and wherein said second supply means additionally includes means for sensing the temperature and pressure of the air within said pressure tank, said control means initiating operation of said compressor means and said heater means to bring said air in said pressure tank to a predetermined pressure and temperature whereby said heated air can be admitted to said sterilization chamber, said control means additionally operating said controllable pressure relief valve means to maintain the pressure within said sterilization chamber below a predetermined value.

9. A method for sterilizing items in a sterilization chamber comprising the steps of:

(A) sealing the sterilizing chamber with the items therein, (B) producing in the sterilizing chamber a vacuum at a predetermined value, including initiating with a vacuum pumping system a vacuum pumping operation when the sterilizing chamber is sealed, monitoring the vacuum in the sterilizing chamber and isolating said vacuum pumping system from the sterilizing chamber when the vacuum reaches a predetermined level, (C) producing a refrigerant in gaseous form and liquefying said gaseous refrigerant, (D) enabling for a predetermined time said refrigerant in liquid form to expand into the sterilizing chamber under vacuum through an expansion valve thereby to reduce rapidly the temperature of any items within the sterilizing chamber, said refrigerant being liquid nitrogen, (E) producing the nitrogen in gaseous form by delivering air from the atmosphere under pressure to a direct air-to-nitrogen conversion system and by accumulating molecular nitrogen from the conversion system, and (F) venting the sterilizing chamber to raise the pressure therein to atmospheric pressure whereby the door can be opened.

10. A method as recited in claim 9 wherein the expansion of nitrogen within the sterilization chamber begins said isolation of the vacuum pumping system.

11. A method as recited in claim 9 wherein said venting step begins after the predetermined time during which the refrigerant expands in the sterilization chamber and comprises the steps of admitting heated gas under pressure to said sterilization chamber to raise rapidly the temperature of the items therein and venting the sterilization chamber if the pressure therein exceeds a predetermined pressure.

12. A method as recited in claim 11 wherein the step of admitting heated gas under pressure to the sterilization chamber includes compressing air in a pressure tank that is controllably isolated from the sterilization chamber and heating the air in the pressure tank to a predetermined pressure.

13. A method as recited in claim 12 wherein said venting step includes monitoring the pressure within the sterilization chamber during the admission of the heated air and opening a venting valve when the pressure in the sterilization chamber reaches a predetermined pressure.

* * * * *